(12) United States Patent
Hahn

(10) Patent No.: US 8,039,019 B2
(45) Date of Patent: Oct. 18, 2011

(54) PHARMACEUTICAL FORMULATION CONTAINING A BIGUANIDE AND AN ANGIOTENSIN ANTAGONIST

(75) Inventor: Elliot F. Hahn, North Miami Beach, FL (US)

(73) Assignee: Andrx Labs, LLC, Davie, FL (US)

( * ) Notice: Subject to any disclaimer, the term of this patent is extended or adjusted under 35 U.S.C. 154(b) by 54 days.

(21) Appl. No.: 12/535,833

(22) Filed: Aug. 5, 2009

(65) Prior Publication Data

US 2009/0297600 A1    Dec. 3, 2009

Related U.S. Application Data

(62) Division of application No. 11/628,066, filed as application No. PCT/US2005/018939 on May 27, 2005, now Pat. No. 7,588,779.

(60) Provisional application No. 60/575,259, filed on May 28, 2004.

(51) Int. Cl.
  *A61K 9/20*    (2006.01)
  *A61K 31/44*    (2006.01)
  *A61K 31/41*    (2006.01)
  *A61K 31/155*    (2006.01)

(52) U.S. Cl. ........ 424/464; 514/342; 514/381; 514/635; 514/866

(58) Field of Classification Search ................ 514/342, 514/381, 635, 824, 866; 424/464
See application file for complete search history.

(56) References Cited

U.S. PATENT DOCUMENTS

| | | |
|---|---|---|
| 5,196,444 A | 3/1993 | Naka et al. |
| 5,534,534 A | 7/1996 | Makino et al. |
| 5,650,170 A | 7/1997 | Wright et al. |
| 5,705,517 A | 1/1998 | Naka et al. |
| 6,099,859 A | 8/2000 | Cheng et al. |
| 6,099,862 A | 8/2000 | Chen et al. |
| 6,682,759 B2 | 1/2004 | Lim et al. |
| 7,588,779 B2 | 9/2009 | Hahn |
| 2001/0024659 A1 | 9/2001 | Chen et al. |
| 2004/0034065 A1 | 2/2004 | Allison et al. |
| 2004/0106660 A1 | 6/2004 | Kositprapa et al. |
| 2004/0161462 A1 | 8/2004 | Kositprapa et al. |
| 2004/0219209 A1 | 11/2004 | Chen et al. |
| 2005/0226928 A1 | 10/2005 | Lodin et al. |

FOREIGN PATENT DOCUMENTS

| | | |
|---|---|---|
| WO | WO9947125 | 9/1999 |
| WO | WO0215933 | 2/2002 |

OTHER PUBLICATIONS

Graffeo, M., International Search Report, PCT/US05/18939, Mar. 9, 2006.
Graffeo, M., Written Opinion of the International Searching Authority, PCT/US05/18939, Mar. 9, 2006.
http://en.wikipedia.org/wiki/Biguanide (2007).

*Primary Examiner* — Kevin E Weddington
(74) *Attorney, Agent, or Firm* — Florek & Endres PLLC

(57) ABSTRACT

A pharmaceutical dosage form comprising a controlled release component comprising an antihyperglycemic drug in combination with a second component comprising a angiotensin antagonist is herein disclosed and described.

24 Claims, No Drawings

PHARMACEUTICAL FORMULATION CONTAINING A BIGUANIDE AND AN ANGIOTENSIN ANTAGONIST

CROSS REFERENCE TO RELATED APPLICATIONS

The present application is a divisional application of U.S. patent application Ser. No. 11/628,066, which was filed on Nov. 28, 2006 now U.S. Pat. No. 7,588,779. U.S. patent application Ser. No. 11/628,066 was a U.S. National Stage filing of International Patent Application No. PCT/US05/18939, which was filed on May 27, 2005 and which claimed the benefits of U.S. Provisional Patent Application Ser. No. 60/575,259, filed on May 28, 2004.

BACKGROUND OF THE INVENTION

The present invention relates to a pharmaceutical dosage form comprising an antihyperglycemic drug, in combination with a second drug. More specifically, the present invention relates to an oral dosage form comprising a biguanide, e.g., metformin or buformin or a pharmaceutically acceptable salt thereof e.g., metformin hydrochloride or the metformin salts described in U.S. Pat. Nos. 3,957,853 and 4,080,472, which are incorporated herein by reference in combination with an angiotensin antagonist as described in U.S. Pat. Nos. 5,196,444; 5,534,534; 5,703,110; and 5,705,517 also incorporated herein by reference.

Many techniques have been used to provide controlled and extended-release pharmaceutical dosage forms in order to maintain therapeutic serum levels of medicaments and to minimize the effects of missed doses of drugs caused by a lack of patient compliance.

For example, extended release tablets have been described which have an osmotically active drug core surrounded by a semi-permeable membrane. These tablets function by allowing the aqueous components of a fluid such as gastric or intestinal fluid to permeate the coating membrane and dissolve the active ingredient so the resultant drug solution can be released through a passageway in the coating membrane. Alternatively, if the active ingredient is insoluble in the permeating fluid, it can be pushed through the passageway by an expanding agent such as a hydrogel. Some representative examples of these osmotic tablet systems can be found in U.S. Pat. Nos. 3,845,770; 3,916,899; 4,034,758; 4,077,407 and 4,783,337. U.S. Pat. No. 3,952,741 teaches an osmotic device wherein the active agent is released from a core surrounded by a semipermeable membrane only after sufficient pressure has developed within the membrane to burst or rupture the membrane at a weak portion of the membrane.

The basic osmotic device described in the above cited patents have been refined over time in an effort to provide greater control of the release of the active ingredient. For example, U.S. Pat. Nos. 4,777,049 and 4,851,229 describe osmotic dosage forms comprising a semipermeable wall surrounding a core. The core contains an active ingredient and a modulating agent wherein the modulating agent causes the active ingredient to be released through a passageway in the semipermeable membrane in a pulsed manner. Further refinements have included modifications to the semipermeable membrane surrounding the active core such as varying the proportions of the components that form the membrane, e.g. U.S. Pat. Nos. 5,178,867, 4,587,117 and 4,522,625, or increasing the number of coatings surrounding the active core, e.g., U.S. Pat. Nos. 5,650,170 and 4,892,739.

Certain controlled or sustained release formulations that employ antihyperglycemic drugs such as metformin hydrochloride have been limited to the use of an expanding or gelling agent to control the release of the drug from the dosage form. This limited research is exemplified by the teachings of WO 96/08243 and by the product insert for GLUCOPHAGE™ XR, which is a controlled release metformin HCl product commercially available from Bristol-Myers Squibb Co.

Angiotensin antagonists have been described in U.S. Pat. Nos. 5,196,444; 5,534,534 and 5,705,517. The therapeutic value of these compounds in combination therapy has further been described in published PCT application WO 0215933. However, none of these patents, or the publication describe a dosage form having the advantages of the subject invention.

Angiotensin antagonists are compounds functioning to control the renin-angiotensin system as well as being clinically useful for the treatment of circulatory diseases such as hypertensive diseases, heart diseases (e.g. hypercardia, heart failure, cardiac infarction, etc.), strokes, cerebral apoplexy, etc. These compounds are required to have potent angiotensin II receptor antagonistic activity and to exert strong oral and long-lasting angiotensin II antagonist action. Several 2-substituted benzimidazole derivatives possessing highly angiotensin II receptor antagonistic activity as well as exerting strong oral and long-lasting angiotensin II antagonistic and anti-hypertensive action have been developed. These compounds are potent angiotensin II antagonists that are of value in the treatment of circulatory system diseases such as hypertensive diseases, heart diseases, strokes, nephritis, etc.

Also known in the art is WO 99/47125 and U.S. Pat. No. 6,099,862 that disclose a metformin osmotic tablet coated with an immediate release coating containing an antihyperglycemic or a hypoglycemic drug.

Although the prior art teaches pharmaceutical dosage formulations that contain both an antihyperglycemic compound and an angiotensin antagonist, the present invention provides numerous benefits over the prior art teachings as will be described below.

SUMMARY OF THE INVENTION

The present invention relates to a pharmaceutical dosage form comprising a first active drug, preferably an antihyperglycemic drug, in combination with a second active drug. The second active drug may be any drug useful in combination therapy with the first active drug. In one embodiment, the first active drug is a biguanide and the second active drug is an angiotensin antagonist.

In certain embodiments, the second active drug may be selected from antidiabetic agents, cardiovascular agents, antilipemic agents, or antiplatelet agents.

The term antidiabetic agent may include, but would not be limited to biguanides (i.e., Metformin, Buformin, Phenformin), sulfonylureas (i.e., Acetohexamide, Carbutamide, Chlorpropamide, Glibornuride, Gliclazide, Glimepiride, Glipizide, Gliquidone, Glisoxepid, Glyburide, Glybuthiazole, Glybuzole, Glyhexamide, Glymidine, Glypinamide, Phenbutamide, Tolazamide, Tolbutamide, Tolcyclomide) thiazolidinediones (i.e., Piogliatazone, Rosiglitazone, Troglitazone), beta andrenergic blockers, and other antidiabetics such as acarbose, calcium mesoxalate, miglitol, nateglinide, repaglinide, voglibose.

The term cardiovascular agent may include, but would not be limited to, alpha andrenergic agonists that include, but are not limited to, Adrafinil, Adrenalone, Amidephrine, Apraclonidine, Budralazine, Clonidine, Cyclopentamine, Dexmedetomidine, Dimetofrine, Dipivefrin, Ecabapide, Ephedrine, Epinephrine, Fenoxazoline, Guanabenz, Guanfacine, Hydroxyamphetamine, Ibopamine, Indanazoline, Isometheptene, Mephentermine, Metaraminol, Methoxamine, Methylhexaneamine, Midodrine, Mivazerol, Modafinil, Moxonidine, Naphazoline, Norepinephrine, Norfenefrine, Octodrine, Octopamine, Oxymetazoline, Phenylephrine Hydrochloride, Phenylpropanolamine, Phenylpropylmethylamine, Pholedrine, Propylhexedrine, Pseudoephedrine, Rilmenidine, Synephrine, Talipexole, Tetrahydrozoline, Tiamenidine, Tramazoline, Tuaminoheptane, Tymazoline, Tyramine, and Xylometazoline.

Beta andrenergic agonists include but are not limited to Albuterol, Bambuterol, Bitolterol, Carbuterol, Clenbuterol, Clorprenaline, Denopamine, Dixoethedrine, Dopexamine, Ephedrine, Epinephrine, Etafedrine, Ethylnorepinephrine, Fenoterol, Formoterol, Hexoprenaline, Ibopamine, Isoetharine, Isoproterenol, Methoxyphenamine, Mabuterol, Metaproterenol, Oxyfedrine, Pirbuterol, Prenalterol, Procaterol, Protokylol, Reproterol, Rimiterol, Ritodrine, Salmeterol, Soterenol, Terbutaline, Tretoquinol, Tulobuterol, and Xamoterol.

Alpha andrenergic blockers include but are not limited to Amosulalol, Arotinolol, Dapiprazole, Doxazosin, Ergoloid Mesylates, Fenspiride, Idazoxan, Indoramin, Labetalol, Monatepil, Naftopidil, Nicergoline, Prazosin, Tamsulosin, Terazosin, Tolazoline, Trimazosin and Yohimbine.

Beta andrenergic blockers include but are not limited to Acebutolol, Alprenolol, Amosulalol, Arotinolol, Atenolol, Befunolol, Betaxolol, Bevantolol, Bisoprolol, Bopindolol, Bucindolol, Bucumolol, Bufetolol, Bufuralol, Bunitrolol, Bupranolol, Butidrine Hydrochloride, Butofilol, Carazolol, Carteolol, Carvedilol, Celiprolol, Cetamolol, Cloranolol, Dilevalol, Esmolol, Indenolol, Labetalol, Landiolol, Levobunolol, Mepindolol, Metipranolol, Metoprolol, Moprolol, Nadolol, Nadoxolol, Nebivolol, Nifenalol, Nipradilol, Oxprenolol, Penbutolol, Pindolol, Practolol, Pronethalol, Propanolol, Sotalol, Sulfinalol, Talinolol, Tertatolol, Tilisolol, Timolol, Toliprolol and Xibenolol.

Antiarrhythmics include but are not limited to Acebutolol, Acecainide, Adenosine, Ajmaline, Alprenolol, Amiodarone, Aprindine, Arotinolol, Atenolol, Azimilide, Bevantolol, Bidisomide, Bretylium Tosylate, Bucumolol, Bufetolol, Bunaftine, Bunitrolol, Bupranolol, Butidrine Hydrochloride, Butobendine, Capobenic Acid, Carazolol, Carteolol, Cifenline, Cloranolol, Disopyramide, Dofetilide, Encainide, Esmolol, Flecainide, Hydroquinidine, Ibutilide, Indecainide, Indenolol, Ipratropium Bromide, Landiolol, Lidocaine, Lorajmine, Lorcainide, Meobentine, Mexiletine, Moricizine, Nadoxolol, Nifenalol, Oxprenolol, Penbutolol, Pentisomide, Pilsicainide, Pindolol, Pirmenol, Practolol, Prajmaline, Procainamide Hydrochloride, Pronethalol, Propafenone, Propranolol, Pyrinoline, Quinidine, Sematilide, Sotalol, Talinolol, Tedisamil, Tilisolol, Timolol, Tocainide, Verapamil and Xibenolol.

Calcium channel blockers include but are not limited to Arylalkylamines: Bepridil, Clentiazem, Diltiazem, Fendiline, Gallopamil, Mibefradil, Prenylamine, Semotiadil, Terodiline, Verapamil; Dihydropyridine Derivatives: Amlodipine, Aranidipine, Bamidipine, Benidipine, Cilnidipine, Efonidipine, Elgodipine, Felodipine, Isradipine, Lacidipine, Lercanidipine, Manidipine, Nicardipine, Nifedipine, Nilvadipine, Nimodipine, Nisoldipine, Nitrendipine; Piperazine Derivatives: Cinnarizine, Dotarizine, Flunarizine, Lidoflazine, Lomerizine; and others: Bencyclane, Etafenone, Fantofarone, Monatepil, and Perhexiline.

Inotropic agents include but are not limited to Digoxin, Milrinone, Dobutamine, and Dopamine.

Vasodilators include but are not limited to Amotriphene, Benfurodil Hemisuccinate, Benziodarone, Chloracizine, Chromonar, Clobenfurol, Clonitrate, Cloricromen, Dilazep, Droprenilamine, Efloxate, Erythrityl Tetranitrate, Etafenone, Fendiline, Hexestrol Bis (β-diethylaminoethyl) ether, Hexobendine, Itramin Tosylate, Khellin, Lidoflazine, Mannitol Hexanitrate, Nitroglycerin, Pentaerythritol Tetranitrate, Pentrinitrol, Perhexiline, Pimefylline, Prenylamine, Propatyl Nitrate, Trapidil, Tricromyl, Trimetazidine, Trolnitrate Phosphate and Visnadine.

Vasopressors include but are not limited to Antihypotensive: Amezinium Methyl Sulfate, Angiotensin Amide, Dopamine, Dimetofrine, Etifelmin, Etilefrin, Gepefrine, Metaraminol, Methoxamine, Midodrine, Norepinephrine, Pholedrine and Synephrine.

The term antiplipemic agents may include, but would not be limited to bile acid sequesterants, fibric acid derivatives, HMG CoA reductase inhibitors, and nicotinic acid.

Bile Acid Sequesterants include but are not limited to Cholestyramine Resin, Cholesevelam Hydrochloride, Colestipol, and Polidexide.

Fibric Acid Derivatives include but are not limited to Bezafibrate, Binifibrate, Ciprofibrate, Clinofibrate, Clofibrate, Clofibric Acid, Etofibrate, Fenofibrate, Gemfibrozil, Pirifibrate, Ronifibrate, Simfibrate and Theofibrate.

HMG CoA Reductase inhibitors include but are not limited to Atorvastatin, Cerivastatin, Fluvastatin, Lovastatin, Pravastatin Sodium and Simvastatin.

Nicotidine Acid Derivatives include but are not limited to Acipimox, Aluminum Nicotinate, Niceritrol, Nicoclonate, Nicomol, and Oxiniacic Acid.

Other Antilipemic agents include but are not limited to Acifran, Benfluorex, β-Benzalbutyramide, Carnitine, Chonodroitin Sulfate, Clomestrone, Detaxtran, Dextran Sulfate Sodium, Eicosapentaenoic Acid, Eritadenine, Ezetimibe, Furazabol, Meglutol, Melinamide, γ-Oryzanol, Pantethine, Pentaerythritol Tetraacetate, α-Phenylbutyramide, Pirozadil, Probucol, β-Sitosterol, Sultosilic Acid, Tiadenol, Triparanol, and Xenbucin.

The term antiplatelet agents may include, but would not be limited to Tirofiban, Dipyridamole, Anagrelide, Epoprostanol, Eptifibatide, Clopidrogel, Cilostazole and Triclopidine.

The foregoing objectives are met by a dosage form comprising a first and second active drug, wherein the first active drug is formulated as a controlled release core, preferably an osmotic tablet, with or without a gelling or expanding polymer. The second active ingredient may be part of the controlled release core or it may be combined with the controlled release core in a manner that provides for immediate release of the second active ingredient. For example, the second active ingredient can be incorporated into a membrane that is applied to the core or the second active ingredient may be applied to a coated or uncoated controlled release core.

In some embodiments, the dosage form may also comprise a capsule containing a controlled release tablet of the first drug and an immediate release tablet of the second drug, a controlled release tablet of the first drug and a controlled release tablet of the second drug, a controlled release tablet of the first drug and an immediate release particles of the second drug, a controlled release tablet of the first drug and a controlled release particles of the second drug, a controlled release tablet of the first drug and immediate release granules of the second drug, a controlled release tablet of the first drug and controlled release granules of the second drug, a controlled release tablet of the first drug and immediate release pellets of the second drug, a controlled release tablet of the first drug and controlled release pellets of the second drug.

In one embodiment the second active drug, which may be an angiotensin antagonist is provided as an immediate release formulation in the dosage form whereas the antihyperglycemic component is provided as a controlled release formulation in the dosage form. This immediate release portion of the formulation should provide peak plasma levels ($T_{max}$) of up to about 24 hours preferably up to about 12 hours, and further preferred up to about 8 hours, while the controlled release portion of the formulation may provide peak plasma levels ($T_{max}$) of up to about 24 hours preferably up to about 12 hours, and further preferred up to about 8 hours of the antihyperglycemic component.

Preferably, the dosage form according to the subject invention may be administered once a day, preferably with or after a meal, and most preferably with or after the evening meal. The subject dosage form can provide therapeutic levels of the drug throughout the day with peak plasma levels ($T_{max}$) of the antihyperglycemic drug being obtained between and up to about 24 hours after administration.

It is an object of the present invention to provide a dosage form comprising a first active drug, which is formulated to provide a controlled or sustained release delivery. Preferably, the first active drug is an antihyperglycemic compound. The present invention further provides for a second active drug, which preferably is an angiotensin antagonist. The novel dosage form described herein provides for delivery of first and second active drugs such that the bioavailability of either drug is not decreased by the presence of food.

It is a further object of the present invention to provide a dosage form, as described above, comprising delivery of a first active drug as a controlled or sustained release formulation for an antihyperglycemic compound, wherein said controlled or sustained release mechanism is not regulated by an expanding polymer, in combination with delivery of a second active drug by immediate release comprising an angiotensin antagonist.

It is a further object of the present invention to provide a dosage form, as described above, comprising delivery of a first active drug as a controlled or sustained release formulation for an antihyperglycemic compound, wherein said controlled or sustained release mechanism is not regulated by an expanding polymer, in combination with delivery of a second active drug by controlled release comprising an angiotensin antagonist.

It is also a further object of the present invention to provide a dosage form as described above, comprising delivery of a first active drug as a controlled or sustained release formulation for an antihyperglycemic compound in combination with delivery of a second active drug by immediate release comprising an angiotensin antagonist that can provide continuous and non-pulsating therapeutic levels of said antihyperglycemic drug to an animal or human in need of such treatment up to a twenty-four hour period. In certain embodiments the subject invention provides therapeutic levels over an eight hour to twenty-four hour period.

It is an additional object of the present invention to provide a dosage form comprising delivery of a first active drug as a controlled or sustained release formulation for an antihyperglycemic compound in combination with delivery of a second active drug by immediate release comprising an angiotensin antagonist that obtains peak plasma levels of the antihyperglycemic compound up to approximately 24 hours. In certain embodiments, the approximately peak plasma levels of the antihyperglycemic compound occur in up to about 12 hours. In yet another embodiment peak, plasma levels of the antihyperglycemic compound occur in approximately 1-12 hours after administration. In certain embodiments, the peak plasma levels of an angiotensin antagonist occur in approximately up to 8 hours after dosing. In certain embodiments, the peak plasma levels of an angiotensin antagonist occur in approximately up to 6 hours after dosing. In certain embodiments, the peak plasma levels of an angiotensin antagonist occur in approximately up to 4 hours after dosing. In certain embodiments, the peak plasma levels of an angiotensin antagonist occur in approximately 1-4 hours after dosing.

It is an additional object of the present invention to provide a dosage form comprising delivery of a first active drug as a controlled or sustained release formulation for an antihyperglycemic compound in combination with delivery of a second active drug by controlled release comprising an angiotensin antagonist that obtains peak plasma levels of the angiotensin antagonist that obtains peak plasma levels of the antihyperglycemic compound up to approximately 24 hours. In certain embodiments the approximately peak plasma levels of the antihyperglycemic compound occur in up to about 12 hours. In yet another embodiment, peak plasma levels of the antihyperglycemic compound occur in approximately 1-12 hours after administration. In certain embodiments, the peak plasma levels of an angiotensin antagonist occur in approximately up to 8 hours after dosing. In certain embodiments, the peak plasma levels of an angiotensin antagonist occur in approximately up to 6 hours after dosing. In certain embodiments, the peak plasma levels of an angiotensin antagonist occur in approximately up to 4 hours after dosing. In certain embodiments, the peak plasma levels of an angiotensin antagonist occur in approximately 1-4 hours after dosing.

It is also an object of the present invention to provide a dosage form comprising a first active drug as a controlled or sustained release pharmaceutical core tablet having only a homogeneous osmotic core wherein the osmotic core component may be made using ordinary tablet compression techniques.

It is a further object of the present invention to provide a dosage form comprising an antihyperglycemic drug as a controlled or sustained release component and an angiotensin antagonist as an immediate release component, wherein not less than 85% of the total amount of the angiotensin antagonist is released from the dosage form within 60 minutes or less.

The foregoing objectives are met by a dosage form comprising a first and second active drug, wherein the first active drug is formulated as a controlled release core, preferably an osmotic tablet, with or without a gelling or expanding polymer.

The second active ingredient may be part of the controlled release core or it may preferably be combined with the controlled release core in a manner that provides for immediate release of the second active ingredient. For example, the second active ingredient can be incorporated into a membrane that is applied to the core or the second active ingredient may be applied to a coated or uncoated controlled release core.

DETAILED DESCRIPTION OF THE INVENTION

The subject invention concerns a pharmaceutical formulation or dosage form comprising a first active drug comprising an antihyperglycemic drug in combination with a second active drug comprising an angiotensin antagonist. Preferably, the antihyperglycemic drug is a biguanide, e.g., metformin or buformin or a pharmaceutically acceptable salt thereof. The antihyperglycemic drug is delivered in a controlled release manner from a tablet core. In one embodiment, controlled release of the antihyperglycemic drugs occurs from an osmotic tablet core with or without a gelling or swelling polymer. The tablet core should include the antihyperglycemic drug and at least one pharmaceutically acceptable excipient. In one embodiment of the present invention the tablet core includes the antihyperglycemic drug, a binding agent and an absorption enhancer, and the tablet core is preferably coated with a polymeric coating to form a membrane around the tablet and drilled to create one passageway through the membrane on each side of the tablet. The second active drug comprises an angiotensin antagonist, and is preferably applied to the membrane of the tablet core and provides for either immediate or controlled release of said angiotensin antagonist.

The term, antihyperglycemic drugs as used in this specification, refers to drugs that are useful in controlling or managing noninsulin-dependent diabetes mellitus (NIDDM). Antihyperglycemic drugs include the biguanides such as metformin, phenformin or buformin or the like, and pharmaceutically acceptable salts, isomers or derivatives thereof.

The term angiotensin antagonist as used in this specification refers to drugs that are useful for controlling or managing NIDDM. These include, but are not limited to, valsartan, losartan, candesartan, eprosartan, irbesartan, olmesartan, tasosartan, and telmisartan or the like, and pharmaceutically acceptable salts, isomers or derivatives thereof.

The term controlled release refers to the spectrum of delivery techniques in pharmaceutical formulations. These may include, but would not be limited to, sustained release, delayed release, targeted delivery, modified release, rapid release, or any other technique in which the dosage form affects the release of the drug.

The term binding agent refers to any conventionally known pharmaceutically acceptable binder such as polyvinyl pyrrolidone, hydroxypropyl cellulose, hydroxyethyl cellulose, hydroxypropyl methylcellulose, ethylcellulose, polymethacrylate, polyvinylalcohol, waxes and the like. Mixtures of the aforementioned binding agents may also be used. The preferred binding agents are water soluble materials such as polyvinyl pyrrolidone having a weight average molecular weight of 25,000 to 3,000,000. The binding agent may comprise approximately about 0 to about 40% of the total weight of the core and preferably about 3% to about 15% of the total weight of the core. In one embodiment, the use of a binding agent in the core is optional.

In a preferred embodiment, the core may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauiyl sulfate, sodium taurocholate and polysorbate 80, chelating agents such as citric acid, phytic acid, ethylenediamine tetraacetic acid (EDTA) and ethylene glycol-bis(β-aminoethyl ether)-N,N,N,N-tetraacetic acid (EGTA). The core may comprise approximately 0 to about 20% of the absorption enhancer based on the total weight of the core and the most preferably about 2% to about 10% of the total weight of the core.

In one embodiment of the present invention, which does not employ a gelling or swelling polymer, the core of the present invention is preferably formed by granulating an antihyperglycemic drug with a binding agent and compressing the granules with the addition of a lubricant and absorption enhancer into a tablet. The core may also be formed by dry granulating the core ingredients by passing them through a roller compactor and compressing the granules with the addition of a lubricant into tablets. Direct compression may also be employed for tabletting. The tablets may be manufactured by other commonly known granulation procedures that are known in the art. Additionally, other excipients such as lubricants, pigments or dyes may also be employed in the formulation of the subject invention.

The term gelling or swelling polymer refers to polymers that gel, swell or expand in the presence of water or biological fluids. Representative examples of gelling or swelling polymers are high molecular weight hydroxpropyl methylcellulose (such as METHOCEL® K100M, which is commercially available from Dow Chemical) and high molecular weight polyethylene oxides (such as POLYOX WSR 301, WSR 303 or WSR COAGULANT). Other gelling or swelling polymers are described in U.S. Pat. No. 4,522,625 (which is incorporated herein by reference).

The core formed as described herein, can be coated with a membrane or sustained release coating. Materials that are useful in forming the membrane or sustained release coating are ethylcellulose, cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate and cellulose acetate butyrate. Other suitable polymers are described in U.S. Pat. Nos. 3,845,770; 3,916,899; 4,008,719; 4,036,228 and 4,612,008 (which are incorporated herein by reference). The most preferred membrane or sustained release coating material is cellulose acetate comprising an acetyl content of 39.3 to 40.3%, and is commercially available from Eastman Fine Chemicals.

In an alternative embodiment, the membrane or sustained release coating can include one of the above-described polymers and a flux-enhancing agent. The flux enhancing agent can increase the volume of fluid imbibed into the core to enable the dosage form to dispense substantially all of the antihyperglycemic drug through the passageway and/or the porous membrane. The flux-enhancing agent can be a water-soluble material or an enteric material. Examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methycellulose, hydroxypropyl methylcellulose phthalate, cellulose acetate phthalate, polyvinyl alcohols, methacrylic acid copolymers, poloxamers (such as LUTROL F68, LUTROL F127, LUTROL F108, which are commercially available from BASF) and mixtures thereof A preferred flux-enhancer is PEG 400.

The flux enhancer may also be a drug that is water soluble such as metformin or its pharmaceutically acceptable salts, or the flux enhancer may be a drug that is soluble under intestinal conditions. If the flux enhancer is a drug, the present dosage form has the added advantage of providing an immediate release of the drug that has been selected as the flux enhancer.

The flux enhancing agent comprises approximately 0 to about 40% of the total weight of the coating, most preferably about 2% to about 20% of the total weight of the coating. The flux enhancing agent dissolves or leaches from the membrane or sustained release coating to form paths in the membrane or sustained release coating, which enables fluid to enter the core and dissolve the active ingredient.

The membrane or sustained release coating may also be formed using a commonly known excipient such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and the like. Depending on the particular plasticizer, amounts from about 0 to about 25%, and preferably about 2% to about 15% of the plasticizer can be used based upon the total weight of the membrane or sustained release coating.

Generally, the membrane or sustained release coating around the core will comprise from about 1% to about 5% and preferably about 2% to about 3% based upon the total weight of the core and coating.

In a preferred embodiment, the membrane or sustained release coating surrounding the core further comprises a passageway that will allow for controlled release of the drug from the core. As used herein the term passageway includes an aperture, orifice, bore, hole, weakened area or an erodible element such as a gelatin plug that erodes to form an osmotic passageway for the release of the antihyperglycemic drug from the dosage form. Passageways used in accordance with the subject invention are well known and are described in U.S. Pat. Nos. 3,845,770; 3,916,899; 4,034,758; 4,077,407; 4,783,337 and 5,071,607.

Independent of the antihyperglycemic is a second active drug. In one embodiment the preferred second drug is an angiotensin antagonist. This second active drug may be formulated to provide an immediate release of the angiotensin antagonist. In one embodiment of the present invention the angiotensin antagonist is applied in the form of a layer to a controlled or sustained released core comprising the antihyperglycemic drug as a layer using a binder and other conventional pharmaceutical excipients such as absorption enhancers, surfactants, plasticizers, antifoaming agents and combinations of the foregoing. An absorption enhancer may be present in the angiotensin antagonist layer in an amount up to about 30% w/w in comparison to the weight of the angiotensin antagonist. A binding agent may be present in an amount up to 150% w/w of the angiotensin antagonist. A second active drug immediate release formulation may be incorporated into a single dosage form by coating onto the membrane or sustained release coating of the dosage form by conventional methods. Alternatively, it may be incorporated by any pharmaceutically acceptable method into a single dosage form with the first active drug. The incorporation of the second active drug may be performed by, but would not be limited to, the processes selected from the group consisting of drug layering, coating, lamination, dry compression, deposition and printing.

When the angiotensin antagonist is coated onto a membrane or sustained release coating of an osmotic tablet core, the angiotensin antagonist should be applied from a coating solution or suspension that employs an aqueous solvent, an organic solvent or a mixture of an aqueous and an organic solvent. Typical organic solvents include acetone, isopropyl alcohol, methanol and ethanol. If a mixture of aqueous and organic solvents is employed, the ratio of water to organic solvent should range from 98:2 to 2:98, preferably 50:50 to 2:98. If a mixed solvent system is employed, the amount of binder required for coating the angiotensin antagonist onto the membrane or sustained release coating may be reduced. For example, successful coatings have been obtained from a mixed solvent system where the ratio of binder to angiotensin antagonist is 1:9 to 1:11. Although acceptable coatings can be obtained when the angiotensin antagonist coat is applied directly to the membrane or sustained release coating, a preferred approach is to first coat the membrane or sustained release coating with a seal coat prior to the application of the angiotensin antagonist coating. As used herein a seal coat is a coating that does not contain an active pharmaceutical ingredient and that rapidly disperses or dissolves in water.

The angiotensin antagonist coating solution or suspension may also contain a surfactant and a pore forming agent. A pore forming agent is preferably a water-soluble material such as sodium chloride, potassium chloride, sucrose, sorbitol, mannitol, polyethylene glycol (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers (such as LUTROL F68, LUTROL F127, LUTROL F108, which are commercially available from BASF) and mixtures thereof. In an alternative embodiment, the dosage form of the present invention may also comprise an effective immediate release amount of the antihyperglycemic drug. The effective immediate release amount of antihyperglycemic drug may be coated onto the membrane or sustained release coating of the dosage form or it may be incorporated into the membrane or sustained release coating.

In addition, various diluents, excipients, lubricants, dyes, pigments, dispersants, etc., which are disclosed in Remington's Pharmaceutical Sciences (1995), may be used to optimize the above listed formulations of the subject invention.

Biguanides, such as metformin are commonly administered in dosage forms containing 500 mg, 750 mg, 850 mg, and 1000 mg. Angiotensin antagonists, for example candesartan, are commonly administered in dosage forms containing 4 mg, 8 mg, 16 mg and 32 mg. The present invention is intended to encompass the above listed therapeutic combinations, without providing a specific example of each possible combination of compounds and their respective dosage amounts.

A preferred embodiment the dosage form will have the following composition:

| FIRST ACTIVE DRUG | | |
|---|---|---|
| Core: | Amount (% of core) | |
| drug | 50-98% | (75-95% preferred) |
| binder | 0.1-40% | (3-15% preferred) |
| absorption enhancer | 0-20% | (2-10% preferred) |
| lubricant | 0-5% | (0.5-1% preferred) |
| Coating: | Amount (% of coating) | |
| polymer | 50-99% | (75-95% preferred) |
| flux enhancer | 0-40% | (2-20% preferred) |
| plasticizer | 0-25% | (2-15% preferred) |

| SECOND ACTIVE DRUG | | |
|---|---|---|
| | Amount (% of total dosage form) | |
| drug | 0.1-20% | (1-10% preferred) |
| binder | 0.1-30% | (1-15% preferred) |
| surfactant | 0-20% | (0.1-15% preferred) |
| pore former | 0-25% | (0.1-15% preferred) |
| polymer (optional) | 0-30% | (0.1-20% preferred) |

The dosage forms prepared according to the present invention exhibit the following dissolution profile when tested in a USP Apparatus 2 apparatus at 75 rpm in 900 mL of simulated intestinal fluid (pH 7.5 phosphate buffer) and at 37° C.:

| Time (hours) | % release | |
|---|---|---|
| Release of First Active Drug | | |
| 2 | 0-25% | (0-15% preferred) |
| 4 | 10-45% | (20-40% preferred) |
| 8 | 30-90% | (45-90% preferred) |
| 12 | NLT 50% | (NLT 60% preferred) |
| 16 | NLT 60% | (NLT 70% preferred) |
| 20 | NLT 70% | (NLT 80% preferred) |
| Release of Second Active Drug | | |
| 0.5 | NLT 60% | (NLT 75% preferred) |

NLT = NOT LESS THAN

It has been discovered that the selection of the excipients for use in the angiotensin antagonist component of the dosage form can greatly affect the release characteristics, potency and stability of the angiotensin antagonist. Therefore, in an alternate embodiment of the present invention, the composition of the angiotensin antagonist component of the present invention should be selected so that not less than 85%, preferably not less than 90% and most preferably not less than 95% of the angiotensin antagonist is released from the dosage form within 45 minutes, preferably within 40 minutes and most preferably within 30 minutes when tested according to the United States Pharmacopeia (USP) 26, with Apparatus 1 at 100 rpm, 37° C. and 900 mL of 0.3 M KCl-HCl Buffer, pH 2.0.

A preferred embodiment of the present invention will exhibit pharmacokinetic parameters for the antihyperglycemic drug that are similar to the pharmacokinetic parameters described in Published United States Patent Application Nos. 200100224659; 20040052848; and 20040219209 which are incorporated herein by reference. More specifically an embodiment of the present invention should exhibit a $C_{max}$ of about 45-80%, preferably about 50-75%, of the $C_{max}$ of an equivalent dose of an immediate release antihyperglycemic drug and a $T_{max}$ of about 160 to about 225%, preferably about 170 to about 215, of the $T_{max}$ of an equivalent does of an immediate release of antihyperglycemic drug. Further, an embodiment of the present invention would provide a $C_{max}$ for the antihyperglycemic drug of about 1500 ng/mL to about 3000 ng/mL, based upon administration of a 2000 gm once-a-day dose of antihyperglycemic drug, more preferably about 1700 ng/mL to about 2000 ng/mL based upon administration of a 2000 gm once-a-day dose of antihyperglycemic drug. Still further, an embodiment of the present invention would provide a mean $AUC_{0-24}$ for the antihyperglycemic drug of about 17200 ng·hr/mL to about 33900 ng·hr/mL, based upon administration of a 2000 gm once-a-day dose of antihyperglycemic drug, preferably about 17200 ng·hr/mL to about 26500 ng·hr/mL based upon administration of a 2000 gm once-a-day dose of antihyperglycemic drug.

EXAMPLES

The following are provided by way of example only and are in no means intended to be limiting.

Example 1

A controlled release tablet containing 850 mg of metformin HCl and 16 mg candesartan celexitil is prepared as follows:

| First Active Drug | |
|---|---|
| I. Core | (% composition of core) |
| Metformin HCl | 90.54% |
| Povidone K-30[1], USP | 4.38% |
| Sodium Tribasic Phosphate | 4.58% |
| Magnesium stearate | 0.5% |

[1]approximate molecular weight = 50,000; dynamic viscosity (10% w/v solution at 20° C.) = 5.5-8.5 m Pa s.

(a) Granulation

The metformin HCl is delumped by passing it through a 40 mesh screen and collecting it in a clean, polyethylene-lined container. The povidone (K-30) and sodium tribasic phosphate are dissolved in purified water. The delumped metformin HCl is then added to a top-spray fluidized bed granulator and granulated by spraying the binding solution of povidone and sodium tribasic phosphate under the following conditions: inlet air temperature of 50-70° C.; atomization air pressure of 1-3 bars and spray rate of 10-100 mL/min.

Once the binding solution is depleted, the granules are dried in the granulator until the loss on drying is less than 2%. The dried granules are passed through a Comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

As stated above, the orifice may be formed by any means commonly employed in the pharmaceutical industry.

(c) Seal Coating (Optional)

The core tablet can be seal coated with an Opadry material or other suitable water-soluble material by first dissolving the Opadry material, preferably Opadry Clear, in purified water. The Opadry solution is then sprayed onto the core tablet using a pan coater under the following conditions: exhaust air temperature of 38-42° C.; atomization pressure of 28-40 psi and spay rate of 10-15 mL/min. The core tablet is coated with the sealing solution until a theoretical coating level of approximately 1-2% is obtained.

| II Membrane | (% composition of membrane) |
|---|---|
| Cellulose Acetate (398-10)[2] | 85% |
| Triacetin | 5% |
| PEG 400 | 10% |

[2]acetyl content 39.3-40.3%

(a) Membrane Coating Process

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16-22° C.; atomization pressure of approximately 3 bars and spray rate of 120-150 mL/min. The sealed core tablet is coated until a theoretical coating level of approximately 3% is obtained.

| III. Second Active Drug Layering | (% composition of second component) |
|---|---|
| Canadesartan Cilexetil | 43.5% |
| Tween 80% | 2.0% |
| Hydroxypropyl methylcellulose | 54.5% |

Tween 80 and hydroxpropyl methylcellulose are dissolved in purified water. Canadesartan Cilexetil is then dispersed into this solution. The resulting suspension is then sprayed onto the above-described tablets.

Example 2

A controlled release tablet containing 850 mg of metformin HCl and 16 mg Candesartan Cilexetil is prepared as follows:

First Active Drug

| I. Core | (% composition of core) |
|---|---|
| Metformin HCl | 88.555% |
| Povidone K-90[3], USP | 6.368% |
| Sodium Lauryl Sulfate | 4.577% |
| Magnesium Stearate | 0.5% |

[3]approximate molecular weight = 1,000,000 dynamic viscosity (10% w/v solution at 20° C. = 300-700 m Pa s.

(a) Granulation

The metformin HCl and sodium lauryl sulfate are delumped by passing them through a 40 mesh screen and collecting them in a clean, polyethylene-lined container. The povidone (K-90) is dissolved in purified water. The delumped metformin HCl and sodium lauryl sulfate are then added to a top-spray fluidized bed granulator and granulated by spraying with the binding solution of povidone under the following conditions: inlet air temperature of 50-70° C., atomization air pressure of 1-3 bars and spray rate of 10-100 mL/min.

Once the binding solution is depleted, the granules are dried in the granulator until the loss of drying is less than 2%. The dried granules are passed through a comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

As stated above, the orifice may be formed by any means commonly employed in the pharmaceutical industry.

(c) Seal Coating (Optional)

The core tablet is seal coated with an Opadry material or other suitable water-soluble material by first dissolving the Opadry material, preferably Opadry Clear, in purified water. The Opadry solution is then sprayed onto the core tablet using a pan coater under the following conditions: exhaust air temperature of 38-42° C.; atomization pressure of 28-40 psi and spay rate of 10-15 mL/min. The core tablet is coated with the sealing solution until a theoretical coating level of approximately 2% is obtained.

| II Membrane | (% composition of membrane) |
|---|---|
| Cellulose Acetate (398-10)[4] | 85% |
| Triacetin | 5% |
| PEG 400 | 10% |

[4]acetyl content 39.3-40.3%

(a) Membrane Coating Process

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16-22° C.; atomization pressure of approximately 3 bars and spray rate of 120-150 mL/min. The sealed core tablet is coated until a theoretical coating level of approximately 3% is obtained.

| III. Second Active Drug Layering | (% composition of second component) |
|---|---|
| Candesartan Cilexetil | 43.5% |
| Tween 80 | 2.0% |
| Hydroxypropyl methylcellulose | 54.5% |

Tween 80 and hydroxypropyl methylcellulose are dissolved in purified water. Candesartan Cilexetil is then dispersed into this solution. The resulting suspension is then sprayed onto the above-described tablets.

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A method for treating patients with hypertension, non-insulin-dependent diabetes mellitus or combinations of the forgoing comprising orally administering once-a-day to the patient a solid pharmaceutical dosage form comprising:
   (a) an antihyperglycemic drug which is metformin or a pharmaceutically acceptable salt thereof and at least one pharmaceutically acceptable controlled release excipient; and
   (b) an angiotensin antagonist selected from the group consisting of valsartan, losartan, candesartan, eprosartan, irbesartan, olmesartan, tasosartan, and telmisartan, and pharmaceutically acceptable salts, isomers or derivatives thereof; and wherein said dosage form exhibits the following dissolution profile when tested in a USP type 2 apparatus at 75 rpm in 900 mL of simulated intestinal fluid (pH 7.5 phosphate buffer) and at 37° C.:
   after 0.5 hours not less than 75% of the angiotensin antagonist is released;
   after 2 hours 0-25% of the antihyperglycemic drug is released;
   after 4 hours 10-45% of the antihyperglycemic drug is released;
   after 8 hours 30-90% of the antihyperglycemic drug is released;

after 12 hours not less than 50% of the antihyperglycemic drug is released;
after 16 hours not less than 60% of the antihyperglycemic drug is released; and
after 20 hours not less than 70% of the antihyperglycemic drug is released.

2. The method of claim 1, wherein said angiotensin antagonist is candesartan.

3. The method of claim 1, wherein said dosage form is substantially free from any gelling or expanding polymer.

4. The method of claim 1 wherein said release of said antihyperglycemic drug provides a $T_{max}$ of 8-12 hours.

5. The method of claim 1 wherein said release of the angiotensin antagonist provides a $T_{max}$ of 1-12 hours.

6. The method of claim 1 wherein said release of the angiotensin antagonist provides a $T_{max}$ of 1-4 hours.

7. The method of claim 1, wherein said dosage form exhibits the following dissolution profile when tested in a USP type 2 apparatus at 75 rpm in 900 mL of simulated intestinal fluid (pH 7.5 phosphate buffer) and at 37° C.:
after 2 hours 0-15% of the antihyperglycemic drug is released;
after 4 hours 20-40% of the antihyperglycemic drug is released;
after 8 hours 45-90% of the antihyperglycemic drug is released;
after 12 hours not less than 60% of the antihyperglycemic drug is released;
after 16 hours not less than 70% of the antihyperglycemic drug is released; and
after 20 hours not less than 80% of the antihyperglycemic drug is released.

8. The method of claim 1, wherein said dosage form exhibits the following dissolution profile when tested in a USP type 1 apparatus at 100 rpm in 900 mL of 0.3 M KCl-HCl buffer, pH 2.0 and at 37° C.:
after 45 minutes not less than 85% of the angiotensin antagonist drug is released.

9. The method of claim 1, wherein said dosage form exhibits the following dissolution profile when tested in a USP type 1 apparatus at 100 rpm in 900 mL of 0.3 M KCl-HCl buffer, pH 2.0 and at 37° C.:
after 45 minutes not less than 90% of the angiotensin antagonist drug is released.

10. The method of claim 1, wherein said dosage form exhibits the following dissolution profile when tested in a USP type 1 apparatus at 100 rpm in 900 mL of 0.3 M KCl-HCl buffer, pH 2.0 and at 37° C.:
after 45 minutes not less than 95% of the angiotensin antagonist drug is released.

11. A method for treating patients with hypertension, non-insulin-dependent diabetes mellitus or combinations of the forgoing comprising orally administering once-a-day to the patient an osmotic tablet comprising:
(a) a core comprising:
(i) 50-98% of an antihyperglycemic drug which is metformin or a pharmaceutically acceptable salt thereof;
(ii) 0.1-40% of a binding agent;
(iii) 0-20% of an absorption enhancer; and
(iv) 0-5% of a lubricant;
(b) optionally a seal coat surrounding the core; and
(c) a sustained release membrane comprising:
(i) 50-99% of a polymer;
(ii) 0-40% of a flux enhancer; and
(iii) 0-25% of a plasticizer, said membrane having at least one passageway formed therein for release of the antihyperglycemic drug; and
(d) an angiotensin antagonist which is selected from the group consisting of valsartan, losartan, candesartan, eprosartan, irbesartan, olmesartan, tasosartan, and telmisartan or pharmaceutically acceptable salts, isomers or derivatives thereof; and
wherein said dosage form exhibits the following dissolution profile when tested in a USP type 2 apparatus at 75 rpm in 900 mL of simulated intestinal fluid (pH 7.5 phosphate buffer) and at 37° C.:
after 0.5 hours not less than 75% of the angiotensin antagonist drug is released;
after 2 hours 0-25% of the antihyperglycemic drug is released;
after 4 hours 10-45% of the antihyperglycemic drug is released;
after 8 hours 30-90% of the antihyperglycemic drug is released;
after 12 hours not less than 50% of the antihyperglycemic drug is released;
after 16 hours not less than 60% of the antihyperglycemic drug is released; and
after 20 hours not less than 70% of the antihyperglycemic drug is released.

12. The method of claim 11, wherein said angiotensin antagonist is candesartan.

13. The method of claim 11, wherein said dosage form is substantially free from any gelling or expanding polymer.

14. The method of claim 11 wherein said release of said antihyperglycemic drug provides a $T_{max}$ of 8-12 hours.

15. The method of claim 11 wherein said release of the angiotensin antagonist provides a $T_{max}$ of 1-12 hours.

16. The method of claim 11 wherein said release of the angiotensin antagonist provides a $T_{max}$ of 1-4 hours.

17. The method of claim 11, wherein said dosage form exhibits the following dissolution profile when tested in a USP type 2 apparatus at 75 rpm in 900 mL of simulated intestinal fluid (pH 7.5 phosphate buffer) and at 37° C.:
after 2 hours 0-15% of the antihyperglycemic drug is released;
after 4 hours 20-40% of the antihyperglycemic drug is released;
after 8 hours 45-90% of the antihyperglycemic drug is released;
after 12 hours not less than 60% of the antihyperglycemic drug is released;
after 16 hours not less than 70% of the antihyperglycemic drug is released; and
after 20 hours not less than 80% of the antihyperglycemic drug is released.

18. The method of claim 11, wherein said dosage form exhibits the following dissolution profile when tested in a USP type 1 apparatus at 100 rpm in 900 mL of 0.3 M KCl-HCl buffer, pH 2.0 and at 37° C.:
after 45 minutes not less than 85% of the angiotensin antagonist drug is released.

19. The method of claim 11, wherein said dosage form exhibits the following dissolution profile when tested in a USP type 1 apparatus at 100 rpm in 900 mL of 0.3 M KCl-HCl buffer, pH 2.0 and at 37° C.:
after 45 minutes not less than 90% of the angiotensin antagonist drug is released.

20. The method of claim 11, wherein said dosage form exhibits the following dissolution profile when tested in a USP type 1 apparatus at 100 rpm in 900 mL of 0.3 M KCl-HCl buffer, pH 2.0 and at 37° C.:
after 45 minutes not less than 95% of the angiotensin antagonist drug is released.

21. A method for treating patients with hypertension, non-insulin-dependent diabetes mellitus or combinations of the forgoing comprising orally administering once-a-day to the patient an osmotic tablet, wherein the osmotic tablet comprises:
  (a) a core comprising:
    (i) 50-98% of an antihyperglycemic drug which is metformin or a pharmaceutically acceptable salt thereof;
    (ii) 0.1-40% of a binding agent;
    (iii) 0-20% of an absorption enhancer;
    (iv) 0-5% of a lubricant; and
    (v) an angiotensin antagonist which is selected from the group consisting of valsartan, losartan, candesartan, eprosartan, irbesartan, olmesartan, tasosartan, and telmisartan or pharmaceutically acceptable salts, isomers or derivatives thereof;
  (b) optionally a seal coat surrounding the core; and
  (c) a sustained release membrane comprising:
    (i) 50-99% of a polymer;
    (ii) 0-40% of a flux enhancer; and
    (iii) 0-25% of a plasticizer, said membrane having at least one passageway formed therein for release of the antihyperglycemic drug; and wherein said dosage form exhibits the following dissolution profile when tested in a USP type 2 apparatus at 75 rpm in 900 mL of simulated intestinal fluid (pH 7.5 phosphate buffer) and at 37° C.:
  after 0.5 hours not less than 75% of the angiotensin antagonist drug is released;
  after 2 hours 0-25% of the antihyperglycemic drug is released;
  after 4 hours 10-45% of the antihyperglycemic drug is released;
  after 8 hours 30-90% of the antihyperglycemic drug is released;
  after 12 hours not less than 50% of the antihyperglycemic drug is released;
  after 16 hours not less than 60% of the antihyperglycemic drug is released; and
  after 20 hours not less than 70% of the antihyperglycemic drug is released.

22. The method of claim 21 wherein said core is substantially free from any gelling or expanding polymer.

23. The method of claim 21 wherein said release of said antihyperglycemic drug provides a $T_{max}$ of 8-12 hours.

24. The method of claim 21 wherein said release of the angiotensin antagonist provides a $T_{max}$ of 1-12 hours.

* * * * *